(12) United States Patent
Takayama et al.

(10) Patent No.: US 8,073,706 B2
(45) Date of Patent: Dec. 6, 2011

(54) EXAMINATION RESERVE SYSTEM, MAINTENANCE SERVICE SYSTEM, MEDICAL IMAGING APPARATUS, EXAMINATION RESERVE METHOD, AND MAINTENANCE SERVICE METHOD

(75) Inventors: Takuzo Takayama, Otawara (JP); Yoichi Takada, Otawara (JP); Akihiro Miyauchi, Kuroiso (JP); Mariko Shibata, Yokohama (JP)

(73) Assignee: Kabushiki Kaisha Toshiba, Tokyo (JP)

( * ) Notice: Subject to any disclaimer, the term of this patent is extended or adjusted under 35 U.S.C. 154(b) by 1951 days.

(21) Appl. No.: 10/349,079

(22) Filed: Jan. 23, 2003

(65) Prior Publication Data

US 2003/0139665 A1 Jul. 24, 2003

(30) Foreign Application Priority Data

Jan. 24, 2002 (JP) .................................. 2002-015915

(51) Int. Cl.
*G06Q 10/00* (2006.01)
*G06Q 50/00* (2006.01)
(52) U.S. Cl. .............................................. 705/2; 705/3
(58) Field of Classification Search ................... 705/2–3
See application file for complete search history.

(56) References Cited

U.S. PATENT DOCUMENTS

| | | | | |
|---|---|---|---|---|
| 6,117,079 A | * | 9/2000 | Brackett et al. | 600/437 |
| 6,246,325 B1 | * | 6/2001 | Chittipeddi | 340/540 |
| 6,389,454 B1 | * | 5/2002 | Ralston et al. | 709/204 |
| 6,436,032 B1 | * | 8/2002 | Eto et al. | 600/117 |
| 6,988,074 B2 | * | 1/2006 | Koritzinsky et al. | 705/2 |

FOREIGN PATENT DOCUMENTS

| | | |
|---|---|---|
| JP | 4-18877 | 1/1992 |
| JP | 6-62130 | 3/1994 |
| JP | 9-275531 | 10/1997 |
| JP | 10-320536 | 4/1998 |
| JP | 11-306466 | 11/1999 |
| JP | 2001-84276 | 3/2001 |
| JP | 2001-104835 | 4/2001 |
| JP | 2001-245091 | 9/2001 |
| JP | 2001-265877 | 9/2001 |
| JP | 2001-273361 | 10/2001 |
| JP | 2001-338082 | 12/2001 |
| JP | 2002-1294 | 1/2002 |
| JP | 2002-015069 | 1/2002 |
| WO | WO 96/16506 | 5/1996 |

* cited by examiner

*Primary Examiner* — Sheetal R Rangrej
(74) *Attorney, Agent, or Firm* — Oblon, Spivak, McClelland, Maier & Neustadt, L.L.P.

(57) ABSTRACT

An examination reserve system receipts a reserve request for an examination using a medical imaging apparatus. The examination reserve system receives information concerning a failure from the medical imaging apparatus. When a failure occurs in the medical imaging apparatus, the system lists receipted examination reserve requests.

7 Claims, 11 Drawing Sheets

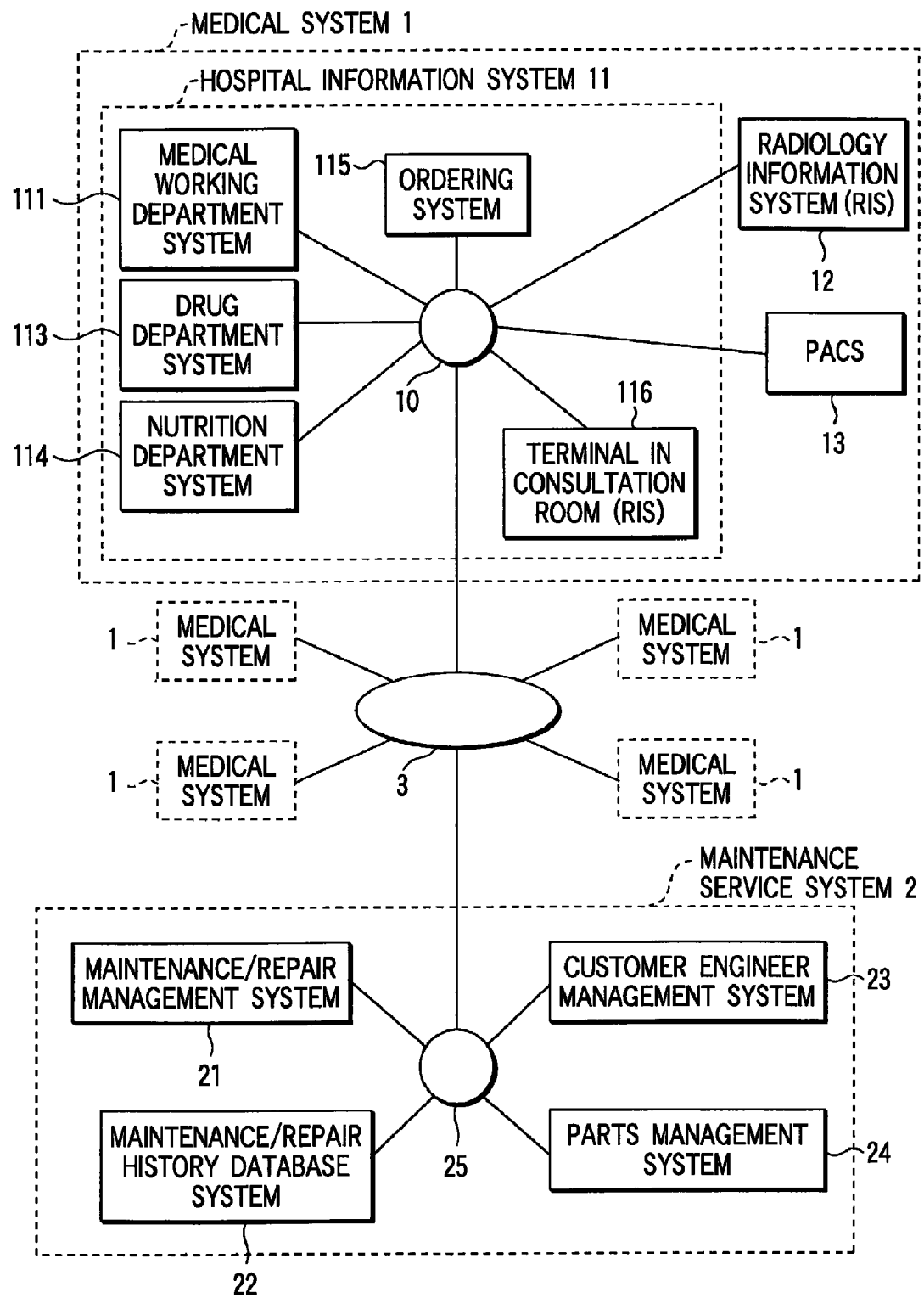
F I G. 1

| PATIENT | REQUEST | RECEIPT | CONDITION |
|---|---|---|---|
| RESERVE LIST | RECEIPT LIST | | FAILURE INF. |

X-RAY DIAGNOSTIC APPARATUS BREAKS DOWN.
EXAMINATION RESERVE REQUEST CANT BE RECEIPTED AFTER 2002/7/11/AM 10:00.

| ID | NAME | CLASS | REGION | WARD | ROOM | RESERVED DATE |
|---|---|---|---|---|---|---|
| 3-0013 | SABURO SATO | PLAIN | CHEST | 3W | FIRST | 2002/7/12/AM 10:00 |

MENU | CANCELLATION NOTICE

FIG. 6

| PATIENT | REQUEST | RECEIPT | CONDITION |
| RESERVE LIST | RECEIPT LIST | FAILURE INF | |

X-RAY DIAGNOSTIC APPARATUS BREAKS DOWN.
EXAMINATION RESERVE REQUEST CAN'T BE RECEIPTED AFTER 2002/7/11/AM 10:00.
CANCELLATION NOTICES ARE TRANSMITTED AUTOMATICALLY BY CLICKING ON
"CANCELLATION NOTICE" BUTTON.

| ID | NAME | CLASS | REGION | WARD | ROOM | RESERVED DATE |
|---|---|---|---|---|---|---|
| 3-0013 | SABURO SATO | PLAIN | CHEST | 3W | FIRST | 2002/7/11/AM 11:00 |
| 0-0024 | HIROSHI SUZUKI | TOMOGRAPHY | CHEST | 5W | SECOND | 2002/7/11/AM 12:00 |
| 0-0037 | TAKASHI EGUCHI | TOMOGRAPHY | CHEST | 5W | FIRST | 2002/7/12/PM 03:00 |
| 2-0027 | JIROU TANAKA | PLAIN | CHEST | 4W | FIRST | 2002/7/12/PM 04:00 |

[ MENU ]      [ CANCELLATION NOTICE ]

FIG. 7

| PATIENT | RECEIPT | CONDITION | | | | |
|---|---|---|---|---|---|---|
| RESERVE LIST | REQUEST | RECEIPT LIST | FAILURE INF. | | | |

X-RAY DIAGNOSTIC APPARATUS CAN'T BE USED IN THE PERIOD 2002/7/11/AM 10:00~2002/7/12/PM 3:00 IN REPAIR. EXAMINATION RESERVE REQUEST CAN'T BE RECEIPTED.
PLEASE INPUT AGAIN REQUEST AFTER 2002/7/12/PM 3:00.

| ID | NAME | CLASS | REGION | WARD | ROOM | RESERVED DATE |
|---|---|---|---|---|---|---|
| 3-0013 | SABURO SATO | PLAIN | CHEST | 3W | FIRST | 2002/7/12/AM 10:00 |

MENU    CANCELLATION NOTICE

F I G. 8

PATIENT RESERVATION TABLE

| PATIENT ID | NAME | CLASS | REGION | WARD | ROOM | RESERVED DATE |
|---|---|---|---|---|---|---|
| 3-0013 | TARO YAMADA | PLAIN | CHEST | 3W | FIRST | 2002/7/11/AM11:00 |
| 0-0024 | HIROSHI SUZUKI | TOMOGRAPHY | CHEST | 5W | FIRST | 2002/7/11/AM12:00 |

FIG. 12A

PHYSICIAN RESERVATION TABLE

| PHYSICIAN ID | NAME | WARD | ROOM | EXAMINATION DATE |
|---|---|---|---|---|
| D0014 | TARO TANAKA | CHEST | 3W | 2002/7/11AM |
| D0023 | SHINJI YOSHIDA | CHEST | 5W | 2002/7/11PM |

FIG. 12B

CONNECTION TABLE

| PATIENT/PHYSICIAN ID | WAY OF CONNECTION | CONNECTION NUMBER |
|---|---|---|
| 3-0013 | FAX | 0123-12-bbbb |
| 3-0014 | Email | xxx@yyy.co.jp |
| 3-0015 | TELEPHONE | 0123-12-aaaa |
| D0014 | Email | kkk@yyy.co.jp |

FIG. 12C

EXAMINATION RESERVE SYSTEM, MAINTENANCE SERVICE SYSTEM, MEDICAL IMAGING APPARATUS, EXAMINATION RESERVE METHOD, AND MAINTENANCE SERVICE METHOD

CROSS-REFERENCE TO RELATED APPLICATIONS

This application is based upon and claims the benefit of priority from the prior Japanese Patent Application No. 2002-15915, filed Jan. 24, 2002, the entire contents of which are incorporated herein by reference.

BACKGROUND OF THE INVENTION

1. Field of the Invention

The present invention relates to an examination reserve system for managing examination reserve requests for a medical imaging apparatus such as an X-ray diagnostic apparatus or X-ray CT apparatus (X-ray computed tomography apparatus), a maintenance service system for a medical imaging apparatus, a medical imaging apparatus, an examination reserve method, and a maintenance service method.

2. Description of the Related Art

When a failure occurs in a medical imaging apparatus such as an X-ray diagnostic apparatus or X-ray CT apparatus (X-ray computed tomography apparatus), examination operation is stopped until the cause of the failure is removed.

Upon reception of a notice of the occurrence of a failure, a maintenance service company dispatches a customer engineer as soon as possible. The dispatched customer engineer is required to check the operation state of each component of the apparatus and estimate the cause of the failure. The customer engineer is also required to cooperate with a user, a person in charge of repair, a person in charge of parts management, and the like and quickly make a repair schedule on the site, if possible.

When a repair schedule is determined, a person in charge of examination reserve management on the hospital side inputs, to an ordering system or examination reserve system, information required to stop the receipt of reserve requests for examinations that use the broken-down medical imaging apparatus until the apparatus recovers from the failure.

In addition, a person in charge in the hospital lists examination reserve requests that have been already receipted until the recovery time, and makes contact with physicians as order sources, patients to be examined, and the like so as to cancel the listed examination reserve requests.

As described above, once a failure occurs in a medical imaging apparatus, the person in charge becomes very busy with work other than routine work. In addition, if a person in charge of examination reserve management is notified of the occurrence of a failure with a delay, an erroneous examination reserve request may be receipted or the examination reserve request may not be canceled in time, resulting in reserving an examination. As a result, the person in charge becomes further busy in handling such problems.

BRIEF SUMMARY OF THE INVENTION

It is an object of the present invention to take a prompt action on examination reserve processing when a failure has occurred in a medical imaging apparatus.

According to the first aspect of the present invention, there is provided an examination reserve system which receipts a reserve request for an examination using a medical imaging apparatus, comprising means for receiving information concerning a failure from the medical imaging apparatus, and means for listing receipted examination reserve requests when a failure has occurred in the medical imaging apparatus.

According to the second aspect of the present invention, there is provided an examination reserve system which receipts a reserve request for an examination using a medical imaging apparatus, comprising means for receiving information concerning a failure indication from the medical imaging apparatus, means for transmitting the information concerning the failure indication to an external maintenance service system via an electronic communication line, means for receiving information concerning a maintenance schedule from the maintenance service system via the electronic communication line, and means for listing receipted examination reserve requests during a maintenance period scheduled by the maintenance schedule.

According to the third aspect of the present invention, there is provided an examination reserve system which receipts a reserve request for an examination using a medical imaging apparatus which acquires image information, comprising means for receiving information concerning a failure indication from the medical imaging apparatus, means for estimating, on the basis of the information concerning the failure indication, a time at which a failure will occur in the medical imaging apparatus, and means for rejecting receipt of an examination reserve request after the estimated time.

According to the fourth aspect of the present invention, there is provided a maintenance service system which is connected, via an electronic communication line, to a medical imaging apparatus and an examination reserve system which receipts a reserve request for an examination using the medical imaging apparatus, comprising means for receiving information concerning a failure from the medical imaging apparatus or the examination reserve system via the electronic communication line, means for forming a plurality of repair schedule plans on the basis of the information concerning the failure, means for transmitting the plurality of repair schedule plans to the examination reserve system via the electronic communication line, means for receiving information concerning a repair schedule plan selected from the plurality of repair schedule plans from the examination reserve system via the electronic communication line, means for determining a repair schedule on the basis of the selected repair schedule plan, and means for transmitting the determined repair schedule to the examination reserve system via the electronic communication line.

According to the fifth aspect of the present invention, there is provided a maintenance service system which is connected, via an electronic communication line, to a medical imaging apparatus and an examination reserve system which receipts a reserve request for an examination using the medical imaging apparatus, comprising means for receiving information concerning a failure from the medical imaging apparatus or the examination reserve system via the electronic communication line, means for forming a repair schedule for the medical imaging apparatus on the basis of the information concerning the failure, and means for transmitting the repair schedule to the examination reserve system via the electronic communication line.

According to the sixth aspect of the present invention, there is provided a medical imaging apparatus connected to an examination reserve system via an electronic communication line, comprising means for detecting occurrence of a failure, and means for transmitting information concerning the failure to the examination reserve system via the electronic communication line when the failure has occurred.

According to the seventh aspect of the present invention, there is provided a medical imaging apparatus connected to an examination reserve system via an electronic communication line, comprising means for detecting occurrence of a failure indication, and means for transmitting information concerning the failure indication to the examination reserve system via the electronic communication line when there is the failure indication.

According to the eighth aspect of the present invention, there is provided an examination reserve method of receipting a reserve request for an examination using a medical imaging apparatus, comprising receiving information concerning a failure from the medical imaging apparatus, listing receipted examination reserve requests when a failure has occurred in the medical imaging apparatus, and transmitting an examination reserve cancellation notice to a terminal of patients and/or physicians corresponding to the listed examination reserve requests.

According to the ninth aspect of the present invention, there is provided an examination reserve method of receipting a reserve request for an examination using a medical imaging apparatus, comprising receiving information concerning a failure from the medical imaging apparatus, rejecting the receipt of an examination reserve request when the failure has occurred, transmitting the information concerning the failure to a maintenance service system, receiving information concerning a repair schedule from the maintenance service system, and canceling rejection of the receipt of an examination reserve request after completion of a repair scheduled by the repair schedule.

According to the 10th aspect of the present invention, there is provided an examination reserve method of receipting a reserve request for an examination using a medical imaging apparatus, comprising receiving information concerning a failure indication from the medical imaging apparatus, transmitting the information concerning the failure indication to a maintenance service system via an electronic communication line, receiving information concerning a maintenance schedule from the maintenance service system via the electronic communication line, listing receipted examination reserve requests during a maintenance period scheduled by the maintenance schedule, and transmitting an examination reserve cancellation notice to a terminal of patients and/or physicians corresponding to the listed examination reserve requests.

According to the 11th aspect of the present invention, there is provided an examination reserve method of receipting a reserve request for an examination using a medical imaging apparatus, comprising receiving information concerning a failure indication from the medical imaging apparatus, transmitting the information concerning the failure indication to a maintenance service system via an electronic communication line, receiving information concerning a maintenance schedule from the maintenance service system via the electronic communication line, listing receipted examination reserve requests during a maintenance period scheduled by the maintenance schedule, and transmitting an examination reserve cancellation notice to a terminal of patients and/or physicians corresponding to the listed examination reserve requests.

According to the 12th aspect of the present invention, there is provided a maintenance service method for a medical imaging apparatus and an examination reserve system which receipts a reserve request for an examination using the medical imaging apparatus, comprising receiving information concerning a failure from the medical imaging apparatus or the examination reserve system via the electronic communication line, forming a plurality of repair schedule plans on the basis of the information concerning the failure, transmitting the plurality of repair schedule plans to the examination reserve system via the electronic communication line, receiving information concerning a repair schedule plan selected from the plurality of repair schedule plans from the examination reserve system via the electronic communication line, determining a repair schedule on the basis of the selected repair schedule plan, and transmitting the determined repair schedule to the examination reserve system via the electronic communication line.

According to the 13th aspect of the present invention, there is provided a maintenance service method for a medical imaging apparatus and an examination reserve system which receipts a reserve request for an examination using the medical imaging apparatus, comprising receiving information concerning a failure indication from the medical imaging apparatus or the examination reserve system via the electronic communication line, forming a plurality of maintenance schedule plans on the basis of the information concerning the failure indication, transmitting the plurality of maintenance schedule plans to the examination reserve system via the electronic communication line, receiving information concerning a maintenance schedule plan selected from the plurality of maintenance schedule plans from the examination reserve system via the electronic communication line, determining a maintenance schedule on the basis of the selected maintenance schedule plan, and transmitting the determined maintenance schedule to the examination reserve system via the electronic communication line.

Additional objects and advantages of the present invention will be set forth in the description which follows, and in part will be obvious from the description, or may be learned by practice of the present invention. The objects and advantages of the invention may be realized and obtained by means of the instrumentalities and combinations particularly pointed out hereinafter.

BRIEF DESCRIPTION OF THE SEVERAL VIEWS OF THE DRAWING

The accompanying drawings, which are incorporated in and constitute a part of the specification, illustrate presently preferred embodiments of the present invention and, together with the general description given above and the detailed description of the preferred embodiments given below, serve to explain the principles of the present invention.

FIG. 1 is a block diagram showing an overall system according to an embodiment of the present invention;

FIG. 6 is a view showing an example of an examination reserve window in the examination reserve system in FIG. 2 at the time of the occurrence of a failure;

FIG. 7 is a view showing an example of a failure information window in the examination reserve system in FIG. 1;

FIG. 8 is a view showing an example of an examination reserve window in the examination reserve system in FIG. 1 at the time of determination of a repair schedule;

FIGS. 12A to 12C are views respectively showing examples of the patient reservation table, physician reservation table, and connection table which are held by the examination reserve system in FIG. 1.

DETAILED DESCRIPTION OF THE INVENTION

Figure 2:
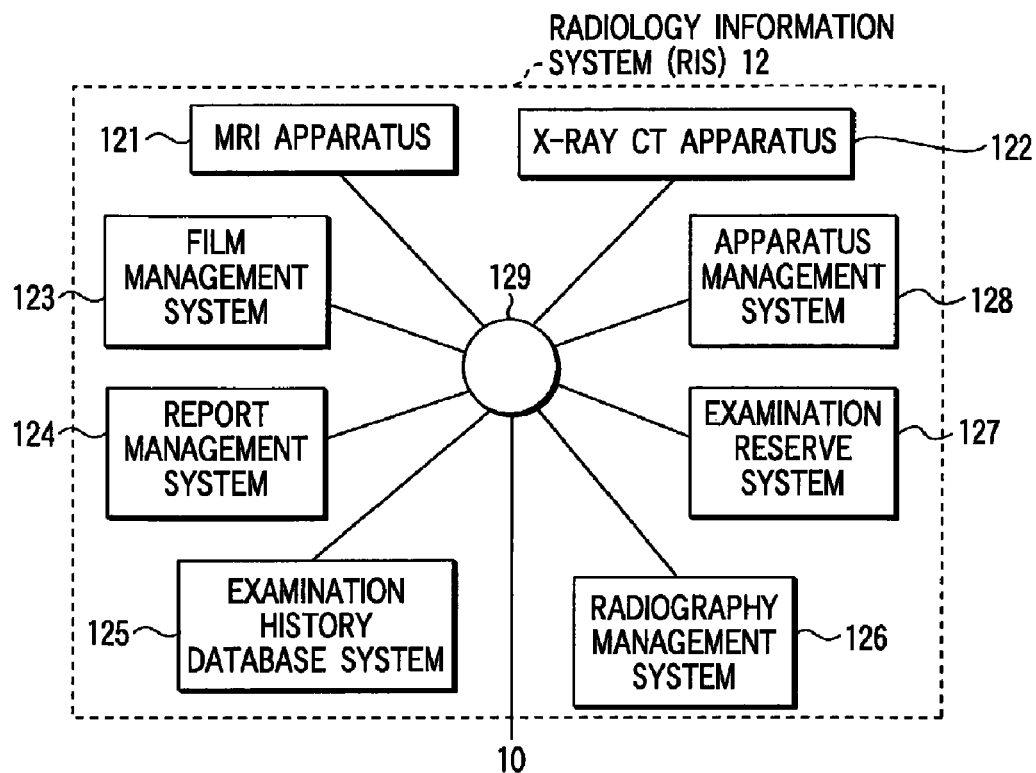
FIG. 2 is a block diagram showing the arrangement of an RIS in FIG. 1.

A preferred embodiment of the present invention will be described below with reference to the several views of the accompanying drawing. FIG. 1 is a block diagram showing the overall arrangement of a system according to this embodiment. A plurality of medical systems 1 are connected to a maintenance service system 2 through a wide area network (WAN) 3. The plurality of medical systems 1 are respectively installed in a plurality of hospital sites. The maintenance service system 2 is installed in a maintenance service company site.

The medical system 1 is comprised of a hospital information system (HIS) 11, radiology information system (RIS) 12, and picture archiving and communications system (PACS) 13 which are connected to each other via a local area network (LAN) 3.

The hospital information system 11 is comprised of a medical working department system 111, a drug department system 113, a nutrition department system 114, an ordering system 115, and a consulting room terminal 116. The ordering system 115 transfers, to proper systems, various information such as patient receipt information, hospitalizing receipt information, examination reserve request information, and drug issue request information which are input through terminals installed in various places.

The radiology information system 12 is a system for improving the efficiency of cumbersome operation in the radiology information department, e.g., examination reserve receipt, examination data input, film management, and document output. As shown in FIG. 2, the radiology information system 12 is comprised of various medical imaging apparatuses (modalities) including an MRI apparatus 121, X-ray CT apparatus 122, digital radio graph (DR) apparatus, digital fluorography (DF) apparatus, nuclear medicine apparatus (NM), ultrasound diagnostic apparatus (US), and electronic endoscope (EES), and the like, a film management system 123, a report management system 124, an examination history database system 125, a radiography management system 126, an examination history database system 125, a radiography management system 126, an examination reserve system 127, and an apparatus management system 128 which are connected to each other via a local area network (LAN) 129.

The examination reserve system 127 has a patient reservation table (see FIG. 12A) in which patient IDs, patient names, classes of examinations, regions to be examined, wards, and rooms are associated with each other, a physician reservation table (see FIG. 12B) in which physician IDs, physician names, wards, and rooms are associated with each other, and a connection table (see FIG. 12C) in which patient/physician IDs, ways of connection, and connection numbers (FAX numbers, telephone numbers, and email addresses) are associated with each other. The examination reserve system 127 performs reservation management and various kinds of notices by using these tables.

Figure 3:
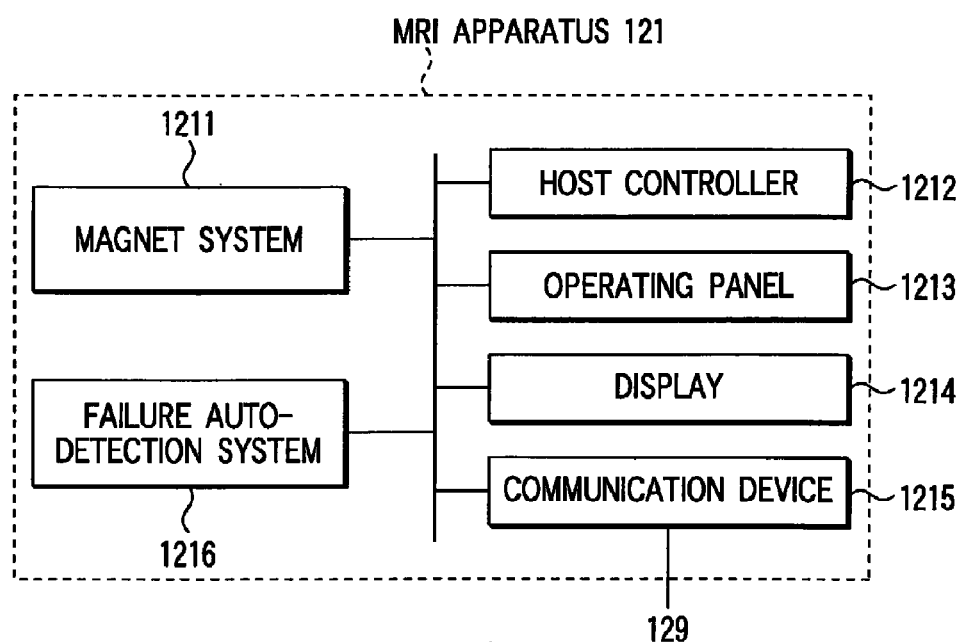
FIG. 3 is a block diagram showing the arrangement of an MRI apparatus in FIG. 2.

As shown in FIG. 3, each modality includes a failure auto-detection system 1216 which performs an automatic check to determine whether a failure or failure indication has occurred, together with basic constituent elements required for the generation of image data. As basic constituent elements, for example, the MRI apparatus 121 includes a magnet system 1211 for generating and acquiring a magnetic resonance signal from an object to be examined, a host controller 1212 for controlling the overall apparatus, an operating panel 1213, a display 1214, and a communication device 1215.

The failure auto-detection system 1216 is provided for each of a plurality of medical imaging apparatuses, and has a function of performing a check suitable for the characteristics of the medical imaging apparatus. For example, the MRI apparatus 121 seals a super-conducting coil in a cryostat together with liquid nitrogen. If the internal temperature does not drop to a predetermined temperature or less, normal imaging operation may not be performed. Assume that the internal temperature is equal to or lower than the predetermined temperature but does not drop to a specific temperature or less which is set to be lower than the predetermined temperature. In this case, it is expected that a failure, i.e., a situation wherein the internal temperature does not drop to the predetermined temperature or less, will occur in the near future. In this case, the failure auto-detection system 1216 is constituted by a temperature sensor, a comparing circuit for comparing the detected temperature with the predetermined temperature (failure detection threshold) for the detection of a failure, and with the specific temperature (failure indicating detection threshold) for the detection of a failure indication, and the like.

In the medical imaging apparatus including an X-ray tube such as an X-ray diagnostic apparatus including the X-ray CT apparatus 122 as a constituent element, for example, an arrangement for detecting a deterioration in the X-ray tube can be used as the failure auto-detection system 1216. In this arrangement, for example, a vibration sensor is attached to the rotating anode element of the X-ray tube or its bearing to detect a vibration frequency at the time of rotation. The detection signal obtained by this vibration sensor is amplified by an amplifier (charge amplifier) and A/D-converted by an A/D converter. The sampled data (vibration signal) is analyzed by a DSP (Digital Signal Processor) to check whether the data represents a normal generation pattern of vibration components, an abnormal pattern (failure pattern) containing clear beat components, or an abnormal indication pattern (failure indication) in which beat components tend to increase although they are not unclear.

The present invention is not limited to this. As an auto-detection scheme for the failure auto-detection system 1216, an arbitrary one of various schemes that are currently implemented may be used.

Referring back to FIG. 1, in the maintenance service system 2, a maintenance repair management system 21 serving as a main system, a maintenance repair history database system 22, a customer engineer management system 23, and a parts management system 24 are connected to each other via a wide area network or local area network 25.

Processes at the time of the occurrence of a failure and at the time of the occurrence of a failure indication according to this embodiment will be described next.

Figure 4:
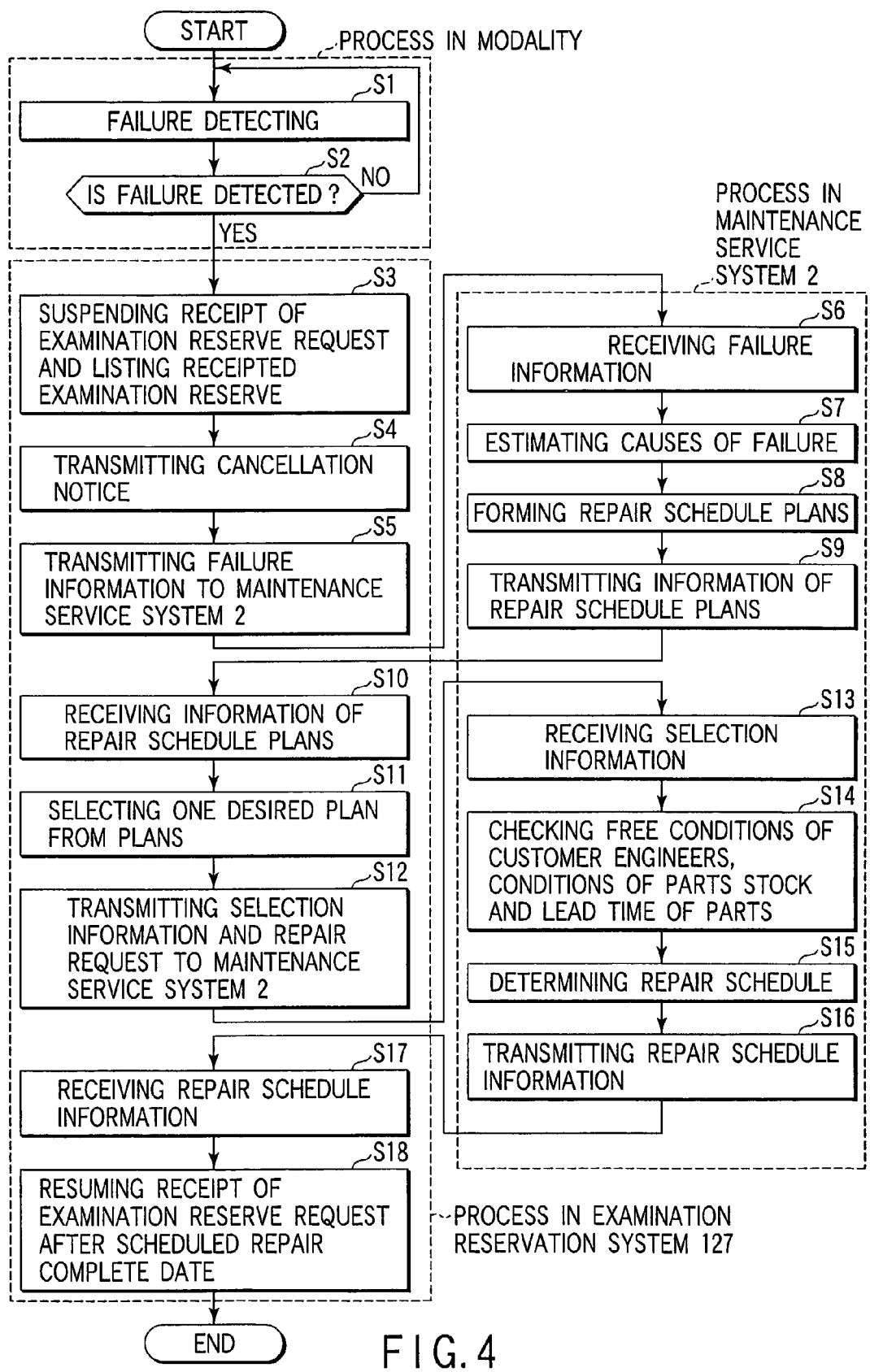
FIG. 4 is a flow chart showing a procedure to be executed at the time of the occurrence of a failure in this embodiment.
Figure 5:
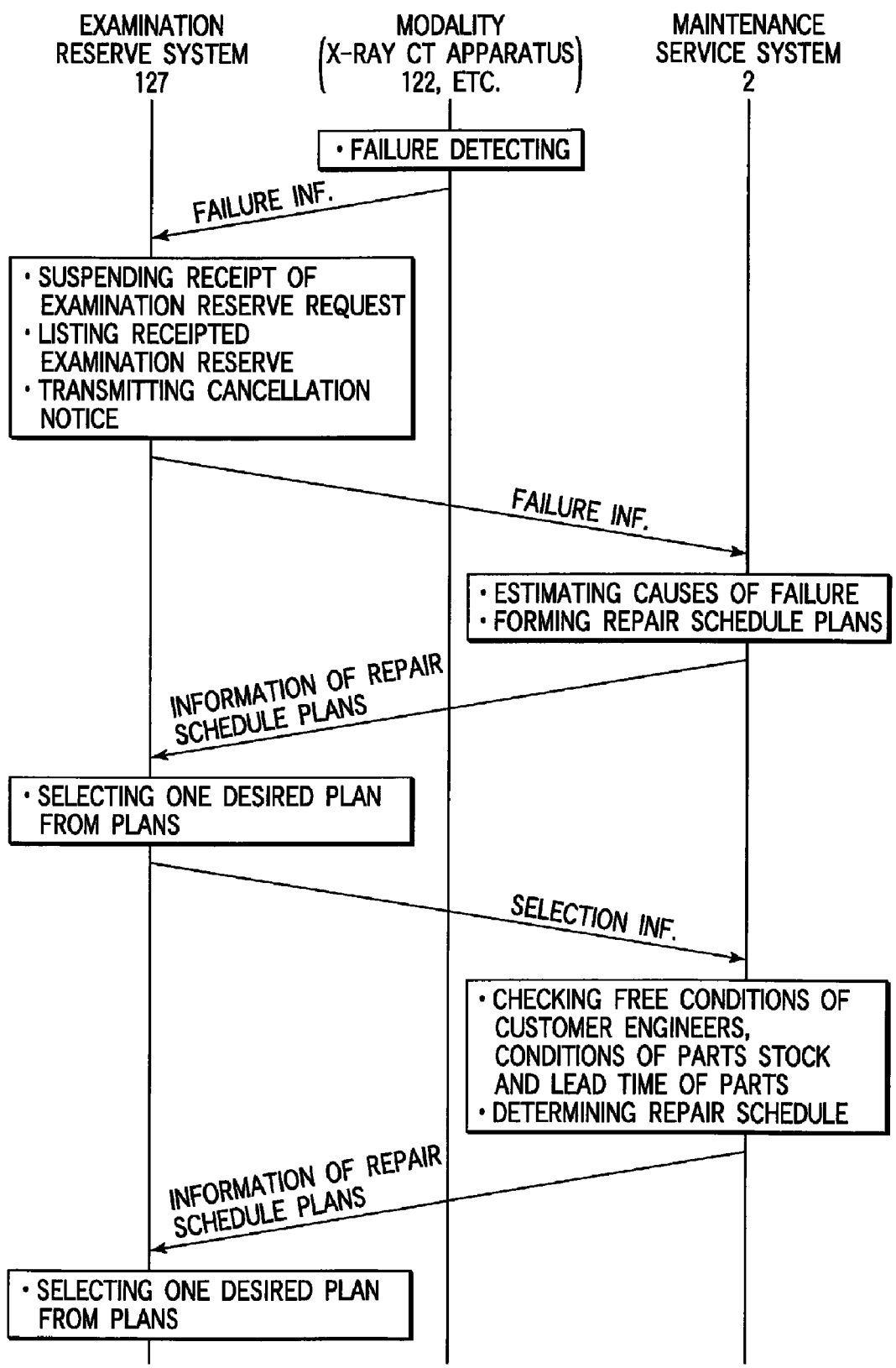
FIG. 5 is a view showing a sequence of information to be transmitted/received between a modality, an examination reserve system, and a maintenance service system, which corresponds to FIG. 4.

FIG. 4 is a flow chart showing a procedure to be executed when a failure occurs. FIG. 5 shows the sequence of information to be transmitted/received between the modality, the examination reserve system, and the maintenance service system, which corresponds to FIG. 4. In this case, the MRI apparatus 121 will be exemplified as the modality. The failure auto-detection system 1216 of the MRI apparatus 121 starts periodically or upon reception of an instruction from the maintenance service system 2. The failure auto-detection system 1216 detects the presence/absence of a failure in, for example, the cryostat of the MRI apparatus 121 by a temperature comparison (S1). If it is determined that a failure has occurred (S2), the communication device 1215 transmits information concerning the occurrence of the failure (failure information) to the examination reserve system 127 via a LAN 10 under the control of the host controller 1212.

Note that the failure auto-detection system 1216 may be installed in the maintenance service system 2. In this case, the failure auto-detection system 1216 of the maintenance service system 2 is caused to perform operation necessary for failure detection for the MRI apparatus 121 by remote control. The failure auto-detection system 1216 of the maintenance service system 2 receives data as a result of the operation necessary for this failure detection from the MRI apparatus 121, and determines whether a failure has occurred.

Upon reception of the failure information, the examination reserve system 127 suspends (rejects) the receipt of subsequent examination reserve requests and lists receipted examination reserve requests (S3).

FIG. 6 shows a receipt window for an examination reserve request in the examination reserve system 127. In this window, the occurrence of a failure in the medical imaging apparatus and the suspension of the receipt of an examination reserve request are displayed in the form, for example, of text messages. As described above, when a failure in the medical imaging apparatus is detected, the corresponding failure information is sent to the examination reserve system 127, leading to quick suspension of the receipt of an examination reserve request.

FIG. 7 shows an example of the listing window of the examination reserve system 127. In this window, a list of receipted examination reserve requests after the occurrence of the failure is displayed together with the "cancellation notice" button. When the "cancellation notice" button is clicked with a pointing device, examination reserve request cancellation notices are automatically transmitted by mail at once to the terminals 116 of patients and physicians corresponding to the listed examination reserve requests (S4). These cancellation notices are made by FAX, Email, telephone, and the like on the basis of the information of the connection table in FIG. 12C.

Figure 9:
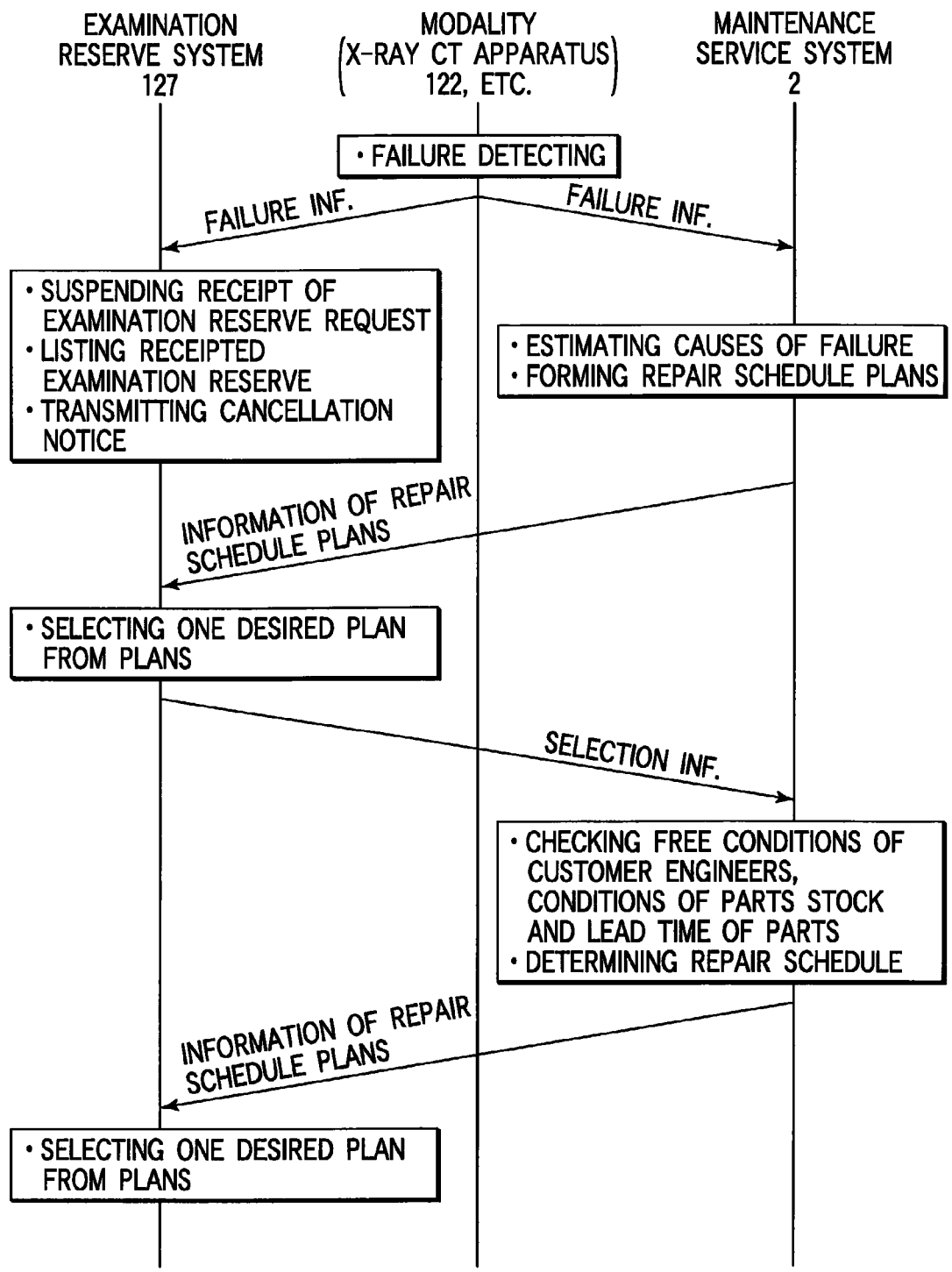
FIG. 9 is a view showing another sequence of information to be transmitted/received between the modality, the examination reserve system, and the maintenance service system, which corresponds to FIG. 4.

The above failure information is transmitted from the MRI apparatus 121 to the maintenance service system 2 via the examination reserve system 127 or directly to the maintenance service system 2 as shown in FIG. 9 (S5). The failure information contains detailed data (e.g., temperature data and its time-varying data). The failure information is received by the maintenance repair management system 21 of the maintenance service system 2 (S6). The maintenance repair management system 21 analyzes the detailed data to estimate the degree of the failure, i.e., at least one cause of the failure (S7). The maintenance repair management system 21 then forms a plurality of different repair schedule plans constituted by parts repair/replacement information, repair time information, cost for the repair, and the like in accordance with the estimated cause (S8). The information of the formed repair schedule plans is transmitted to the medical system 1 (S9).

The received repair schedule plans are sent to the examination reserve system 127 (S10) and displayed in the selection window. A person in charge of apparatus management selects one of the plurality of repair schedule plans and inputs a repair request (S11). The repair schedule plan selection information is transmitted, together with a repair request form, from the examination reserve system 127 to the maintenance service system 2 (S12).

The maintenance repair management system 21 of the maintenance service system 2 receives the repair schedule plan selection information and repair request form (S13) and inquires of the parts management system 24 about information concerning the selected repair schedule plan to check the stock of parts required for the repair, the lead time of pairs, and the like. The maintenance repair management system 21 also inquires of the customer engineer management system 23 in charge of dispatch scheduling of customer engineers to check the date when a customer engineer can be dispatched (S14). The maintenance repair management system 21 specifies the earliest date when parts and a customer engineer become available, and determines the final repair plan including a scheduled repair complete date, a repair method, and the like (S15). The maintenance repair management system 21 then transmits the determined repair schedule information to the medical system 1 (S16).

This repair schedule information is received by the examination reserve system 127 of the medical system 1 (S17). The examination reserve system 127 extracts the scheduled repair complete date in the repair schedule information and resumes the receipt of examination reserve requests after the scheduled repair complete date (S18).

FIG. 8 shows an example of the receipt window for an examination reserve request in the examination reserve system 127. After the scheduled repair complete date information is received, a message that prompts inputting of an examination reserve request after the scheduled repair complete date is displayed as, for example, a text message, together with the suspension period of the receipt of examination reserve requests. In this manner, after the scheduled repair complete date information is received, the date when the suspension of the receipt of examination reserve requests is canceled is displayed.

Figure 10:
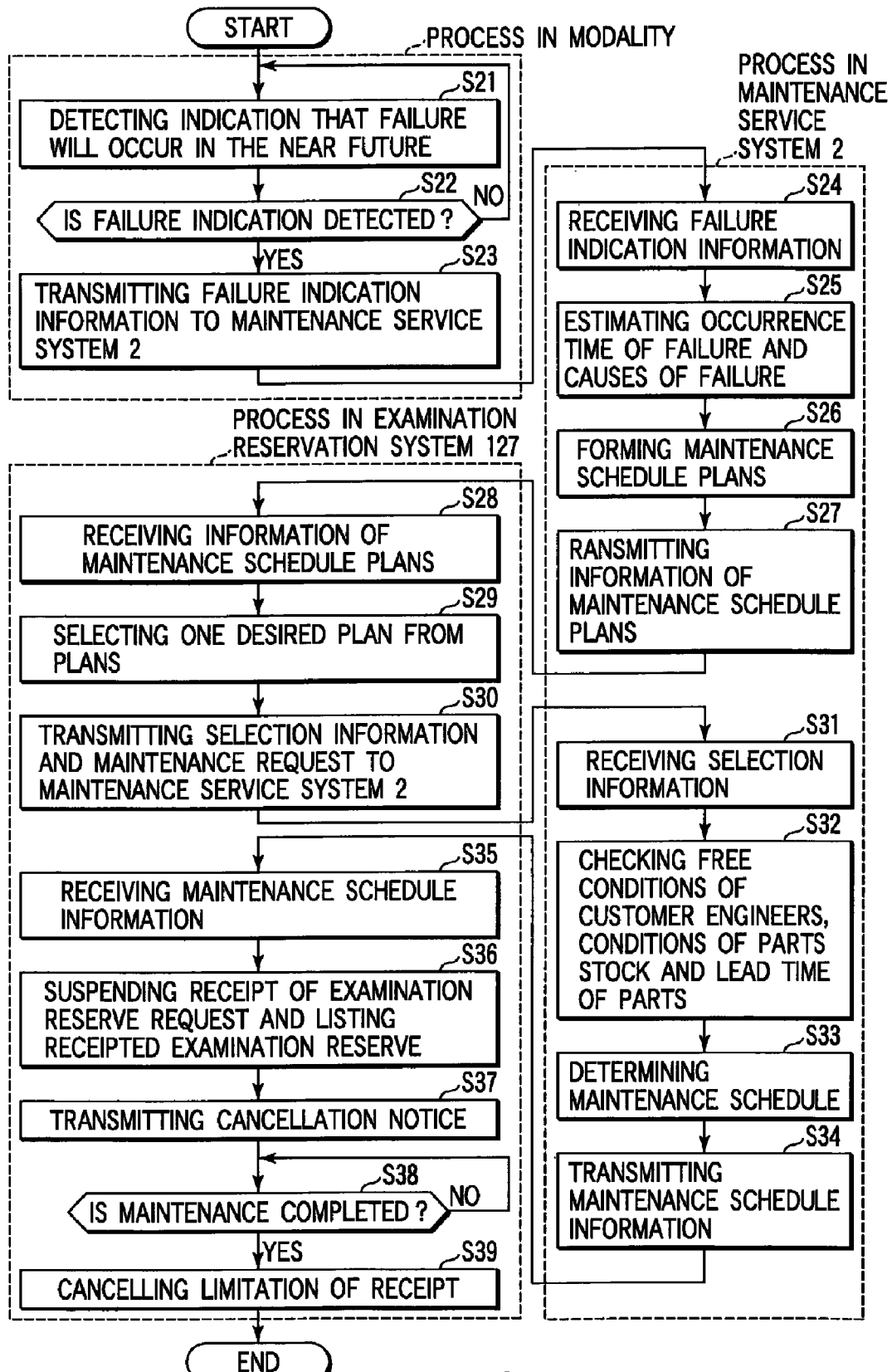
FIG. 10 is a flow chart showing a procedure to be executed at the time of the occurrence of a failure indication in this embodiment.
Figure 11:
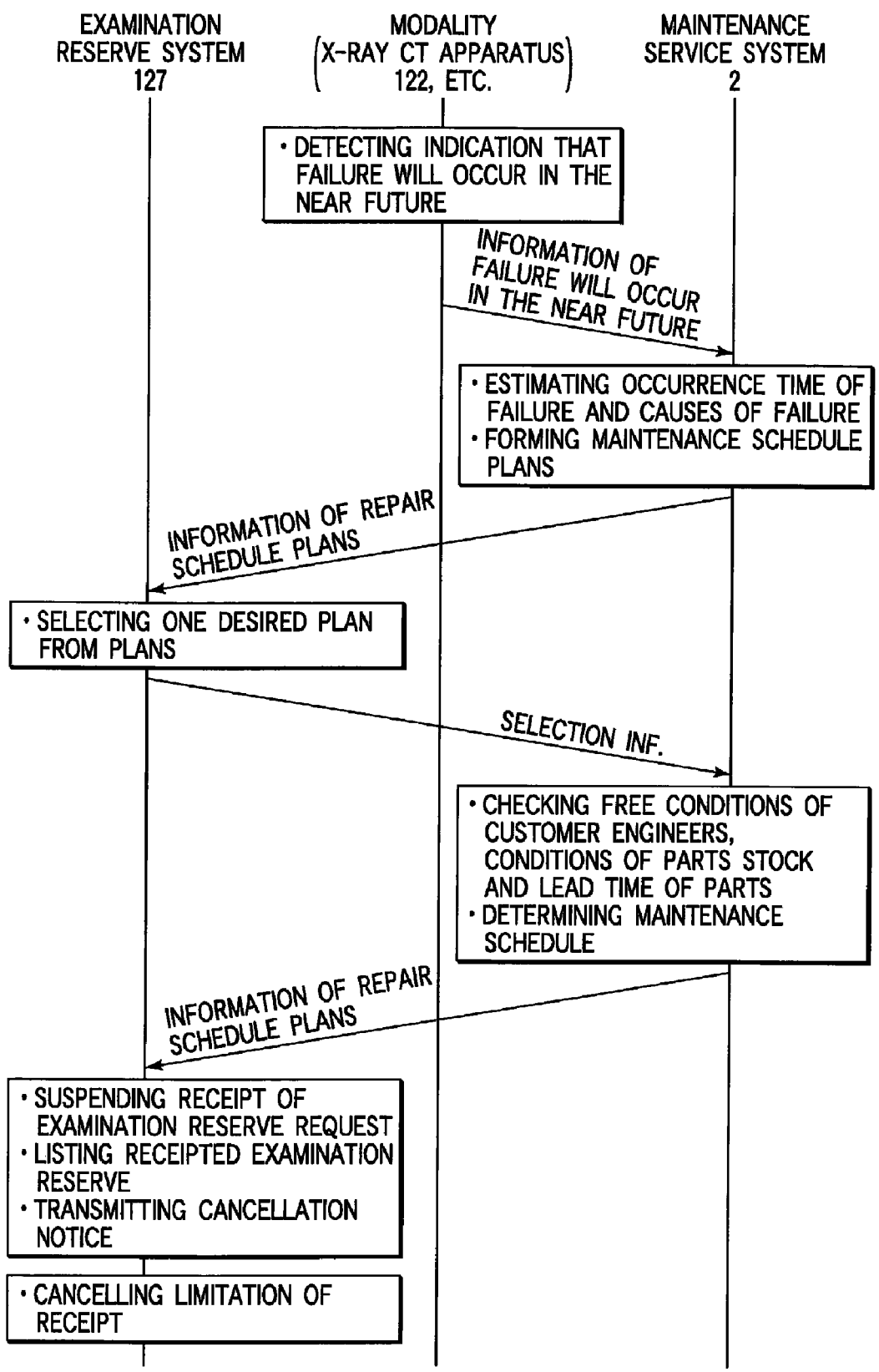
FIG. 11 is a view showing a sequence of information to be transmitted/received between the modality, the examination reserve system, and the maintenance service system, which corresponds to FIG. 10.

FIG. 10 is a flow chart showing a procedure to be executed when a failure indication has occurred. FIG. 11 shows a sequence of information to be transmitted/received between the modality, the examination reserve system, and the maintenance service system, which corresponds to FIG. 10. First of all, the failure auto-detection system 1216 of the MRI apparatus 121 checks, for example, by a temperature comparison whether a failure indication has occurred in the cryostat of the MRI apparatus 121 (S21). If it is determined that there is a failure indication (S22), information concerning the failure indication (failure indication information) is transmitted from the MRI apparatus 121 to the maintenance service system 2 directly or via the ordering system 115 (or the examination reserve system 127) (S23). The failure indication information contains detailed data (e.g., temperature data and its time-varying data). This failure indication information is received by the maintenance repair management system 21 of the maintenance service system 2 (S24). The maintenance repair management system 21 analyzes the detailed data to estimate at least one cause of the failure indication, and estimates the time when the failure indication will surface as a failure, i.e., the time when a failure will actually occur (S25).

Note that the function of "analyzing detailed data to estimate a cause of a failure indication and estimating the time when a failure will actually occurs" which is executed by the maintenance repair management system 21 may be implemented on the medical system 1 side, e.g., in the failure auto-detection system 1216 of the MRI apparatus 121 and the examination reserve system 127. In this case, the examination reserve system 127 can immediately suspend the receipt of examination reserve requests after the estimated failure time.

The maintenance repair management system 21 forms a plurality of different maintenance schedule plans each constituted by maintenance contents (part repair/replacement information), a maintenance period, a cost required for the maintenance, and the like in accordance with at least one estimated cause (S26). The information of the plurality of formed maintenance schedule plans is then transmitted to the medical system 1 (S27).

The received maintenance schedule plans are sent to the examination reserve system 127 (S28) and displayed in the selection window. A person in charge of apparatus management selects one of the plurality of maintenance schedule plans and inputs a maintenance request (S29). The maintenance schedule plan selection information is transmitted, together with a maintenance request form, from the examination reserve system 127 to the maintenance service system 2 (S30).

The maintenance repair management system 21 of the maintenance service system 2 receives the maintenance schedule plan selection information and maintenance request form (S31) and inquires of the parts management system 24 about information concerning the selected maintenance schedule plan to check the stock of parts required for the maintenance, the lead time of pairs, and the like. The maintenance repair management system 21 also inquires of the customer engineer management system 23 in charge of dispatch scheduling of customer engineers to check the date when a customer engineer can be dispatched (S32). The maintenance repair management system 21 specifies the earliest date when parts and a customer engineer become available, and determines the final repair plan including a maintenance method, a maintenance period, and the like (S33). The maintenance repair management system 21 then transmits the determined maintenance schedule information to the medical system 1 (S34).

This maintenance schedule information is received by the examination reserve system 127 of the medical system 1 (S35). The examination reserve system 127 extracts the maintenance period information in the maintenance schedule information and suspends (rejects) the receipt of examination reserve requests during the maintenance period and lists receipted examination reserve requests in the maintenance period (S36).

As in the case shown in FIG. 7, a list of receipted examination reserve requests during the maintenance period is displayed, together with the "cancellation notice" button, in the listing window of the examination reserve system 127. When the "cancellation notice" button is clicked, mail informing the cancellation of the examination reserve requests is automatically transmitted to the terminals 116 of patients and physicians corresponding to the listed examination reserve requests (S37).

When the scheduled maintenance complete information is input to the examination reserve system 127 (S38), the limitation of the receipt of examination reserve requests during the maintenance period is canceled, i.e., the receipt of examination reserve requests during the maintenance period is resumed (S39).

As described above, when a failure indication is detected, the receipt of examination reserve requests during a maintenance period can be suspended immediately after a maintenance schedule is determined.

(Modification)

The present invention is not limited to the above embodiment, and can be variously modified and practiced without departing from the spirit or scope of the invention. The above embodiment includes various stages, and various inventions can be extracted by proper combinations of a plurality of disclosed constituent elements. For example, several constituent elements may be omitted from all the constituent elements in the embodiment.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed is:

1. An examination reserve system which manages, using a patient reservation table that includes a patient name, a region of the patient to be examined, an examination room, and a reservation date, reserve requests for an examination of the patient using a medical imaging apparatus of a hospital, the examination reserve system being provided independently of the medical imaging apparatus and being connectable to the medical imaging apparatus via a network, the system comprising:

means for receiving information concerning a failure from the medical imaging apparatus;

means for automatically suspending receipt of subsequent examination reserve requests and for displaying, using the patient reservation table, previously received examination reserve requests, when receiving the information concerning the failure from the medical imaging apparatus, each examination reserve request including the patient name, the region of the patient to be examined, the examination room, and the reservation date;

means for automatically transmitting an examination reserve cancellation notice to a terminal of patients and/or physicians corresponding to the displayed examination reserve requests via an electronic communication line; and means for receiving, from an external maintenance service system over the network, repair schedule information including a completion date, extracting the completion date from the repair schedule information, and automatically resuming receipt of the examination reserve requests after the completion date.

2. A system according to claim 1, further comprising:

means for transmitting information concerning the failure to the external maintenance service system via an electronic communication line; and means for receiving the repair schedule information from the maintenance service system via the electronic communication line.

3. An examination reserve system which manages, using a patient reservation table that includes a patient name, a region of the patient to be examined, an examination room, and a reservation date, reserve requests for an examination of the patient using a medical imaging apparatus of the hospital, the examination reserve system being provided independently of the medical imaging apparatus and being connectable to the medical imaging apparatus via a network, the system comprising:

means for receiving information concerning a failure indication from the medical imaging apparatus;

means for transmitting the information concerning the failure indication to an external maintenance service system via an electronic communication line;

means for receiving information concerning a maintenance schedule including a completion date, from the maintenance service system via the electronic communication line;

means for automatically suspending receipt of subsequent examination reserve requests and for displaying, using the patient reservation table, previously received examination reserve requests during a maintenance period scheduled by the maintenance schedule, each examination reserve request including the patient name, the region of the patient to be examined, the examination room, and the reservation date;

means for transmitting an examination reserve cancellation notice to a terminal of patients and/or physicians corresponding to the displayed examination reserve requests via an electronic communication line; and means for automatically resuming receipt of the examination reserve requests after the completion date.

4. An examination reserve system which manages, using a patient reservation table that includes a patient name, a region of the patient to be examined, an examination room, and a reservation date, reserve requests for an examination of the patient using a medical imaging apparatus of a hospital which acquires image information, the examination reserve system being provided independently of the medical imaging apparatus and being connectable to the medical imaging apparatus via a network, the system comprising:

means for receiving information concerning a failure indication from the medical imaging apparatus;

means for estimating, on the basis of the information concerning the failure indication, a time at which a failure will occur in the medical imaging apparatus;

means for receiving information concerning a maintenance schedule, including a completion date, from a maintenance service system via an electronic communication line;

means for automatically rejecting receipt of an examination reserve request after the estimated time, each examination reserve request including the patient name, the region of the patient to be examined, the examination room, and the reservation date;

means for transmitting an examination reserve cancellation notice to a terminal of patients and/or physicians corresponding to the examination reserve requests via an electronic communication line; and means for suspending receipt of subsequent examination reserve requests after the completion date.

5. An examination reserve method implemented by an examination reserve system that manages, using a patient reservation table that includes a patient name, a region of the patient to be examined, an examination room, and a reservation date, reserve requests for an examination of the patient using a medical imaging apparatus of a hospital, the examination reserve system being provided independently of the medical imaging apparatus and being connectable to the medical imaging apparatus via a network, the method comprising:

receiving information concerning a failure from the medical imaging apparatus;

automatically suspending receipt of subsequent examination reserve requests and displaying previously received examination reserve requests when receiving the information concerning the failure from the medical imaging apparatus, each examination reserve request including the patient name, the region of the patient to be examined, the examination room, and the reservation date;

transmitting an examination reserve cancellation notice to a terminal of patients and/or physicians corresponding to the displayed examination reserve requests via an electronic communication line; and receiving, over the network from an external maintenance service system repair, schedule information including a completion date, extracting the completion date from the repair schedule information, and automatically resuming receipt of the examination reserve requests after the completion date.

6. An examination reserve method implemented by an examination reserve system, of managing, using a patient reservation table that includes a patient name, a region of the patient to be examined, an examination room, and a reservation date, reserve requests for an examination of the patient using a medical imaging apparatus of a hospital, the examination reserve system being provided independently of the medical imaging apparatus and being connectable to the medical imaging apparatus in a network, the method comprising:

receiving information concerning a failure from the medical imaging apparatus;

automatically suspending receipt of subsequent examination reserve requests when receiving the information concerning the failure;

transmitting the information concerning the failure to a maintenance service system;

transmitting an examination reserve cancellation notice to a terminal of patients and/or physicians corresponding to the examination reserve requests via an electronic communication line;

receiving repair schedule information including a completion date from the maintenance service system;

extracting the completion date from the repair schedule information; and automatically resuming receipt of the examination reserve requests after the completion date.

7. An examination reserve method implemented by an examination reserve system that manages, using a patient reservation table that includes a patient name, a region of the patient to be examined, an examination room, and a reservation date, reserve requests for an examination of the patient using a medical imaging apparatus of a hospital, the examination reserve system being provided independently of the medical imaging apparatus and being connectable to the medical imaging apparatus via a network, the method comprising:

receiving information concerning a failure indication from the medical imaging apparatus;

transmitting the information concerning the failure indication to a maintenance service system via an electronic communication line;

receiving information concerning a maintenance schedule including a completion date from the maintenance service system via the electronic communication line;

automatically suspending receipt of subsequent examination reserve requests and displaying previously received examination reserve requests during a maintenance period scheduled by the maintenance schedule, each examination reserve request including the patient name, the region of the patient to be examined, the examination room, and the reservation date;

transmitting an examination reserve cancellation notice to a terminal of patients and/or physicians corresponding to the displayed examination reserve requests via an electronic communication line; and automatically resuming receipt of the examination reserve requests after the completion date.

\* \* \* \* \*